(12) United States Patent
Fernandes

(10) Patent No.: US 11,327,023 B2
(45) Date of Patent: May 10, 2022

(54) NON-COVALENT COMPLEX-BASED SENSORS

(71) Applicant: Texas Tech University System, Lubbock, TX (US)

(72) Inventor: Gregory Fernandes, Lubbock, TX (US)

(73) Assignee: TEXAS TECH UNIVERSITY SYSTEM, Lubbock, TX (US)

(*) Notice: Subject to any disclaimer, the term of this patent is extended or adjusted under 35 U.S.C. 154(b) by 0 days.

(21) Appl. No.: 16/831,545

(22) Filed: Mar. 26, 2020

(65) Prior Publication Data

US 2020/0309708 A1    Oct. 1, 2020

Related U.S. Application Data

(60) Provisional application No. 62/824,133, filed on Mar. 26, 2019.

(51) Int. Cl.
| | |
|---|---|
| *G01N 21/76* | (2006.01) |
| *G01N 21/64* | (2006.01) |
| *G01N 33/58* | (2006.01) |

(52) U.S. Cl.
CPC ......... *G01N 21/76* (2013.01); *G01N 21/6428* (2013.01); *G01N 33/582* (2013.01); *G01N 2021/6432* (2013.01)

(58) Field of Classification Search
CPC .. G01N 21/76; G01N 33/582; G01N 21/6428; G01N 2021/6432; G01N 31/22
See application file for complete search history.

(56) References Cited

U.S. PATENT DOCUMENTS

| | | | | |
|---|---|---|---|---|
| 5,028,395 A | * | 7/1991 | Sebille | ................ G01N 21/643 422/82.06 |
| 6,485,703 B1 | | 11/2002 | Coté et al. | |

(Continued)

FOREIGN PATENT DOCUMENTS

| | | |
|---|---|---|
| WO | 2006083932 A2 | 8/2006 |
| WO | 2009152102 A2 | 12/2009 |
| WO | 2017105927 A1 | 6/2017 |

OTHER PUBLICATIONS

Lou et al., "A Highly Sensitive and Selective Fluorescent Probe for Cyanide Based on the Dissolution of Gold Nanoparticles and Its Application in Real Samples", 2011, Chem. Eur. J., 17, 9691-9696 (Year: 2011).*

(Continued)

*Primary Examiner* — Jill A Warden
*Assistant Examiner* — Henry H Nguyen
(74) *Attorney, Agent, or Firm* — Loza & Loza LLP; Kevin L. Soules

(57) ABSTRACT

A system, method, and apparatus for sensing analytes comprises assembling a sensor of at least one polymer and at least one fluorophore by mixing the polymer with the fluorophore, exposing the sensor to an analyte, and identifying the presence of the analyte according to a change in fluorescence of the sensor. The sensor can comprise a non-covalent complex of the at least one fluorophore and the at least one polymer. The at least one polymer can comprise a polymer capable of binding a metal ion. The at least one polymer is capable of binding a metal ion comprising an imidazole-containing polymer such as an N-vinylimidazole homo polymer and/or an N-vinylimidazole co-polymer.

4 Claims, 10 Drawing Sheets

(56) References Cited

U.S. PATENT DOCUMENTS

| | | |
|---|---|---|
| 8,268,977 B2 | 9/2012 | Kool et al. |
| 8,344,150 B2 | 1/2013 | Ajayaghosh et al. |
| 8,372,649 B2 | 2/2013 | Ayyapanpillai et al. |
| 8,575,303 B2 | 11/2013 | Gaylord et al. |
| 9,416,155 B2 | 8/2016 | Kool |
| 9,557,337 B2 | 1/2017 | Mehrpouyan et al. |
| 2002/0160411 A1 | 10/2002 | Kool |
| 2005/0064529 A1 | 3/2005 | Kwon |
| 2007/0049761 A1 | 3/2007 | Wilson et al. |
| 2010/0221188 A1* | 9/2010 | Clark ............... G01N 33/66 424/9.6 |
| 2012/0282705 A1* | 11/2012 | Lei ................. G01N 31/227 436/110 |
| 2016/0097754 A1* | 4/2016 | Basu ............... G01N 21/643 436/81 |
| 2018/0364245 A1 | 12/2018 | Martin et al. |

OTHER PUBLICATIONS

Kuchler et al., "Development of a metal-island-coated swelling/shrinking copolymer sensor for measurement of divalent metal ions", 2010, Monatshefte fur Chemie—Chemical Monthly, vol. 141, pp. 131-135 (Year: 2010).*

Rivas et al., "Metal Ion Binding Properties of Poly(N-vinylimidazole)Hydrogels", 1998, Journal of Applied Polymer Science, 67, 1109-1118. (Year: 1998).*

Andersson et al., "Vinylimidazole copolymers: coordination chemistry, solubility, and cross-linking as function of Cu2+ and Zn2+ complexation", 2011, Colloid and Polymer Science, 289, 1361-1372. (Year: 2011).*

Tong et al., "Ratiometric Detection of Cu2+ Using a Luminol-Tb-GMP Nanoprobe with High Sensitivity and Selectivity", 2018, ACS Sustainable Chem. Eng., 6, 9333-9341 (Year: 2018).*

* cited by examiner

NON-COVALENT COMPLEX-BASED SENSORS

CROSS-REFERENCE TO RELATED PATENT APPLICATIONS

This patent application claims the priority and benefit under 35 U.S.C. § 119(e) of U.S. Provisional Patent Application Ser. No. 62/824,133, filed Mar. 26, 2019, entitled "NON-COVALENT-COMPLEX-BASED SENSORS." U.S. Provisional Patent Application Ser. No. 62/824,133 is herein incorporated by reference in its entirety.

TECHNICAL FIELD

Embodiments are generally related to the field of sensors. Embodiments are further related to the field of fluorescent sensors. Embodiments are also related to methods, systems, and devices that use as-received, commercially-available fluorophores for sensing. Embodiments are further related to methods, systems, and devices for environmental and biological monitoring, clinical diagnostics, disease identification, and drug discovery. Embodiments are further related to methods, systems, and devices based on a non-covalent complex of at least one fluorophore and at least one polymer that can bind, and therefore detect, environmentally and biologically important ions (including, but not limited to, $Cu^+$, $Cu^{2+}$, and $Hg^{2+}$). Embodiments are further related to methods, systems, and devices based on a non-covalent complex of at least one fluorophore, at least one polymer, and at least one fluorescence quencher that senses analytes that remove at least one quencher from the complex. Embodiments are further related to methods, systems, and devices based on a non-covalent complex of luminol, an imidazole containing polymer, and $Cu^{2+}$ for enhanced chemiluminescence applications.

BACKGROUND

Modern sensor systems can provide detection of target analytes. Certain sensor systems make use of colorimetric and fluorescent indicators. These sensor technologies have become increasingly popular because of their sensitivity, detection time, and relative simplicity. These sensor systems can be used to sense or image molecules, including cations, anions, cellular components in living humans, and other biological samples, and can be used in other diagnostic applications.

Covalent linking of an analyte binding site and signaling fluorophore is the most popular fluorescent sensor assembly strategy. The most widely used approach in fluorescence sensing is the indicator-spacer-receptor (ISR) approach, wherein the indicator is covalently attached to the receptor (analyte binding site) through a spacer. Analyte binding to the receptor induces a measurable change in fluorescence. A significant limitation of the ISR approach is the difficult synthesis that may be required for covalent linking of the indicator to the receptor. Another significant drawback is that synthetic modification of the indicator can negatively affect critical sensor design criteria such as water solubility, brightness, and emission spectrum. As such, prior art strategies are synthesis-intensive and can negatively impact probe solubility, brightness, and emission wavelength.

Furthermore, the dysregulation of anionic species such as PPi and $H_2S/HS^-/S^{2-}$ are involved in crucial intracellular processes, associated with many diseases such as cancer, chondrocalcinosis, Alzheimer's disease, Down's syndrome, diabetes, and liver cirrhosis. Elements like copper and iodide are essential for human health. $Cu^{2+}$ plays a critical role in cellular respiration, the central nervous system, and acts as a catalytic cofactor for numerous metal enzymes. However, this essential trace element is toxic at higher concentrations, resulting in oxidative stress, liver and kidney damage, and diseases such as Menkes disease, Wilson's disease, and Alzheimer's disease. The environmental poison $CN^-$ causes inhibition of respiration. Excess intake of mercury results in skin discoloration, peripheral neuropathy, and kidney failure.

Practically speaking, this gives rise to significant health risks. For example, corrosion of household plumbing can release copper or other metals into the drinking water. Traditional methods for sensitive detection of environmentally and biologically relevant ions like titration, ICP-MS, electrochemical methods, ion chromatography, gas chromatography, voltammetry, and potentiometry are time consuming and require sophisticated instrumentation.

Accordingly, there is a need in the art for systems and methods that provide synthesis free sensing technology, as disclosed herein, that overcome the aforementioned limitations by using a polymer to non-covalently bind both signaling fluorophore and the analyte.

SUMMARY

The following summary is provided to facilitate an understanding of some of the innovative features unique to the embodiments disclosed and is not intended to be a full description. A full appreciation of the various aspects of the embodiments can be gained by taking the entire specification, claims, drawings, and abstract as a whole.

It is, therefore, one aspect of the disclosed embodiments to provide a method, system, and apparatus for sensing compounds.

It is another aspect of the disclosed embodiments to provide a sensing fluorophore-based complex.

It is another aspect of the disclosed embodiments to provide synthesis-free sensors.

It is another aspect of the disclosed embodiments to provide devices for environmental and biological monitoring, clinical diagnostics, disease identification, and drug discovery.

It is another aspect of the disclosed embodiments to provide a non-covalent complex of at least one fluorophore and at least one polymer that can bind, and therefore detect, environmentally and biologically important ions (including, but not limited to, $Cu^+$, $Cu^{2+}$, and $Hg^{2+}$).

It is another aspect of the disclosed embodiments to provide a non-covalent complex of at least one fluorophore, at least one polymer, and at least one fluorescence quencher that senses analytes that remove at least one quencher from the complex.

It is another aspect of the disclosed embodiments to provide a non-covalent complex of luminol, a polymer, and $Cu^{2+}$ for enhanced chemiluminescence applications.

The aforementioned aspects and other objectives and advantages can now be achieved as described herein. In an exemplary embodiment, a sensing method comprises assembling a sensor comprising at least one polymer and at least one fluorophore by mixing the polymer with the fluorophore, exposing the sensor to an analyte, and identifying the presence of the analyte according to a change in fluorescence of the sensor. In an embodiment, the sensor comprises a non-covalent complex of the at least one fluorophore and the at least one polymer. In an embodiment, the at least one polymer comprises a polymer capable of binding a metal ion. In an embodiment, the at least one polymer capable of binding a metal ion comprises an imidazole-containing polymer. In an embodiment, the at least one polymer comprises at least one of an N-vinylimidazole homo polymer and/or an N-vinylimidazole co-polymer. In an embodiment, assembling the sensor comprising at least one polymer and the at least one fluorophore by mixing the polymer with the fluorophore, further comprises quenching fluorescence of the at least one fluorophore with at least one fluorescence quencher. In an embodiment, the method further comprises removing the at least one fluorescence quencher from the at least one fluorophore and the at least one polymer, thereby restoring fluorescence of the sensor. In an embodiment, the analyte can be suspected to contain at least one of: $Cu^+$, $Cu^{2+}$, and/or $Hg^{2+}$.

In another embodiment, a sensor comprises at least one fluorophore and at least one polymer wherein a change in sensor fluorescence is indicative of the presence of an analyte. In an embodiment, the sensor comprises a non-covalent complex of the at least one fluorophore and the at least one polymer. In an embodiment, the at least one polymer comprises a polymer capable of binding a metal ion. In an embodiment, the at least one polymer comprises an imidazole-containing polymer. In an embodiment, the imidazole-containing polymer comprises at least one of an N-vinylimidazole homo polymer and an N-vinylimidazole co-polymer. In an embodiment the sensor further comprises at least one fluorescence quencher. In an embodiment, fluorescence of the sensor is restored in the presence of at least one analyte that removes the at least one quencher from the sensor. In an embodiment, the analyte comprises at least one of: $Cu^+$, $Cu^{2+}$, and/or $Hg^{2+}$.

In yet another embodiment, a system comprises a non-covalent complex of at least one fluorophore and at least one polymer capable of binding a metal ion, the at least one polymer capable of binding the metal ion further comprising at least one of at least one imidazole-containing polymer, an N-vinylimidazole homopolymer, and an N-vinylimidazole co-polymer. In an embodiment the system further comprises at least one fluorescence quencher. In an embodiment the fluorescence of the sensor is restored in the presence of at least one analyte that removes the at least one fluorescence quencher from the non-covalent complex of at least one fluorophore and the at least one polymer. In an embodiment of the system, the at least one polymer comprises at least one imidazole containing polymer, and the non-covalent complex further comprises luminol and $Cu^{2+}$ wherein the system is configured for chemiluminescence applications.

BRIEF DESCRIPTION OF THE FIGURES

The accompanying figures, in which like reference numerals refer to identical or functionally-similar elements throughout the separate views and which are incorporated in, and form a part of the specification, further illustrate the embodiments and, together with the detailed description, serve to explain the embodiments disclosed herein.

DETAILED DESCRIPTION

Figure 1A:
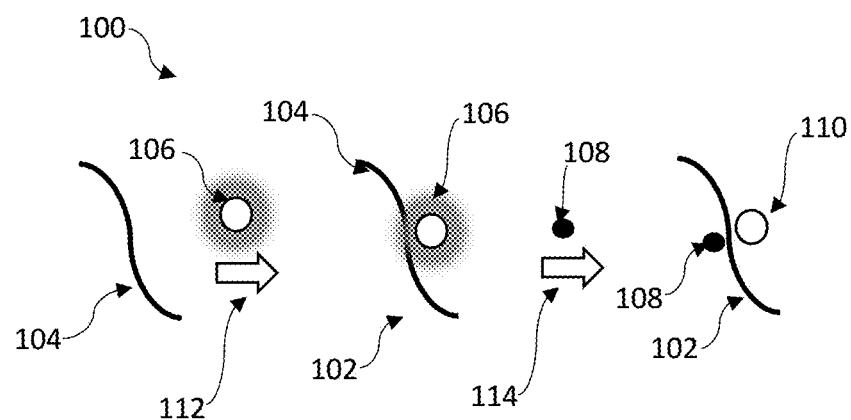
FIG. 1A depicts a schematic diagram of a fluorescence sensor, in accordance with the disclosed embodiments.

The particular values and configurations discussed in the following non-limiting examples can be varied, and are cited merely to illustrate one or more embodiments and are not intended to limit the scope thereof.

Example embodiments will now be described more fully hereinafter with reference to the accompanying drawings, in which illustrative embodiments are shown. The embodiments disclosed herein can be embodied in many different forms and should not be construed as limited to the embodiments set forth herein; rather, these embodiments are provided so that this disclosure will be thorough and complete, and will fully convey the scope of the embodiments to those skilled in the art. Like numbers refer to like elements throughout.

The terminology used herein is for the purpose of describing particular embodiments only and is not intended to be limiting. As used herein, the singular forms "a," "an," and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Throughout the specification and claims, terms may have nuanced meanings suggested or implied in context beyond an explicitly stated meaning. Likewise, the phrase "in one embodiment" as used herein does not necessarily refer to the same embodiment and the phrase "in another embodiment" as used herein does not necessarily refer to a different embodiment. It is intended, for example, that claimed subject matter include combinations of example embodiments in whole or in part.

Unless otherwise defined, all terms (including technical and scientific terms) used herein have the same meaning as commonly understood by one of ordinary skill in the art. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include"), or "containing" (and any form of containing, such as "contains" and "contain") are inclusive or open-ended and do not exclude additional, unrecited elements, or method steps.

The term "or combinations thereof" as used herein refers to all permutations and combinations of the listed items preceding the term. For example, "A, B, C, or combinations thereof" is intended to include at least one of: A, B, C, Aft AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

All of the compositions and/or methods disclosed and claimed herein can be made and executed without undue experimentation in light of the present disclosure. While the compositions and methods of this invention have been described in terms of preferred embodiments, it will be apparent to those skilled in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope, and concept of the invention as defined by the appended claims.

For reference, as used herein, an imidazole containing macromolecule or polymer means a polymer or a macromolecule in which the imidazole ring has been incorporated. The term "quenching" or "fluorescence quenching" as used herein refers to a decrease in fluorescence of the sensor in the presence of a quencher or analyte as compared to the fluorescence of the sensor in the absence of the quencher or analyte. The term "restored" or "turned-on" as used herein refers to an increase in fluorescence of a sensor in the presence of analyte as compared to the fluorescence of a sensor in the absence of analyte. The term "remove," "removing," and "removal" as used herein with respect to a quencher refers to any mechanism or process that results in the quencher no longer being able to quench the fluorescence of the fluorophore, a polymer, and a quencher (FPQ) complex. Furthermore, the term "sensor," as used herein can refer to any variant of the disclosed sensors.

The methods and systems disclosed herein are directed to synthesis free sensor systems that, in a non-limiting sense, comprise one of the following: (i) at least one signaling fluorophore non-covalently bound to a polymer that is also capable of binding an analyte; (ii) an analyte sensing non-covalent complex comprising of at least one signaling fluorophore and at least one fluorescence quencher and a polymer; and/or (iii) a non-covalent complex comprising luminol, an N-vinylimidazole homo, or co-polymer and $Cu^{2+}$. The disclosed facile sensor systems can facilitate environmental and biological monitoring, clinical diagnostics, disease identification, drug discovery, and other sensing applications.

The embodiments provide non-covalent complexes of at least one fluorophore and metal-ion complexing polymer (including, but not limited to imidazole containing polymers) that can sensitively detect the environmentally and biologically important cations $Cu^+$, $Cu^{2+}$, and $Hg^{2+}$ without the need for covalent attachment of analyte binding site to the fluorophore; non-covalent complexes of at least one fluorophore, a metal-ion complexing polymer (including, but not limited to, imidazole containing polymers) and $Cu^{2+}$ that can detect any analyte that can remove $Cu^{2+}$ from the complex (a non-limiting example includes siderophores secreted by microorganisms); non-covalent complexes of at least one fluorophore, a metal-ion complexing polymer (including, but not limited to, imidazole containing polymers) and $Cu^{2+}$ that can detect the environmentally and biologically significant anions $CN^-$, $I^-$, PPi and $H_2S/HS^-/S^{2-}$ via $Cu^{2+}$ displacement; non-covalent complexes of at least one fluorophore, a metal-ion complexing polymer (including, but not limited to, imidazole containing polymers) and $Cu^{2+}$ that can detect enzyme activity based on enhanced or diminished $Cu^{2+}$ chelating abilities of the products of enzyme activity on substrates; and luminol-imidazole-containing-polymer-$Cu^{2+}$ complexes for chemiluminescence-based sensors, biosensors, immunoassays, nucleic acid assays, protein and nucleic acid blotting, and reporter gene-based assays. As used herein, an imidazole containing macromolecule or polymer means a polymer or a macromolecule in which the imidazole ring has been incorporated.

Use of a polymer to non-covalently bind both the signaling fluorophore and the analyte represents a unique feature of the present embodiments. In certain embodiments, fluorophore-polymer ratios that maximize sensitivity towards cationic analytes such as $Cu^{2+}$ and $Hg^{2+}$ are disclosed. Copolymers of N-vinylimidazole and N-vinylpyrrolidone can be used to vary the strength of the $Cu^{2+}$-polymer interaction. This can be used to control sensitivity and selectivity of anion sensing via $Cu^{2+}$ displacement, enable sensitive and specific detection of enzyme activity, and systematically tune metal ion catalytic activity in the luminol- $H_2O_2$ chemiluminescence reaction.

The sensor design strategy disclosed herein overcomes prior art shortcomings, allowing a vast array of commercially available fluorophores to be used, as-received, in sensor construction. Cheap, water-soluble, bright, wavelength-tunable sensors made possible by the disclosed facile sensor assembly strategy will greatly accelerate progress in the fields of biosensing, environmental and bioprocess monitoring, as well as clinical diagnostics and drug discovery.

Furthermore, the new sensing platform disclosed herein can be used for the development of practical in-field detection kits for $H_2O_2$ and environmental poisons such as $Cu^{2+}$, $Hg^{2+}$, and $CN^-$, cancer diagnosis and disease identification via use of in-vitro and in-vivo bioimaging probes for small anionic species such as $CN^-$, $I^-$, PPi and H, $H_2S/HS^-/S_2$, drug discovery through rapid screening of potential protease activity inhibitors, development of diagnostic tools for kinase related diseases using kinase assays and the detection of substrates of enzymes releasing $H_2O_2$ (e.g., glucose and cholesterol).

The methods and systems disclosed herein provide a new approach to sensor design that uses a polymer to non-covalently bind both a signaling fluorophore and an analyte.

FIG. 1A illustrates a method 100 associated with a fluorescence sensor 102, in accordance with the disclosed embodiments. The fluorescence sensor 102 uses a polymer 104 to non-covalently bind a fluorophore 106 and analyte 108. As illustrated in FIG. 1A, the first step is to form the fluorescence sensor 102 by binding the polymer and fluorophore 106, as illustrated by arrow 112. It should be noted that, at this point the fluorophore 106 is fluorescing, as illustrated by the halo surrounding fluorophore 106. The sensor 102 can then be introduced to an environment where the analyte 108 is suspected to be present. If the analyte 108 is present, the analyte 108 binds to the sensor 102 as illustrated by arrow 114. The fluorescence "turns off," as illustrated by non-fluorescing fluorophore 110 (which a skilled artisan will appreciate is the same structure as fluorophore 106), of sensor 102, indicating that the analyte 108 is present.

Figure 1B:
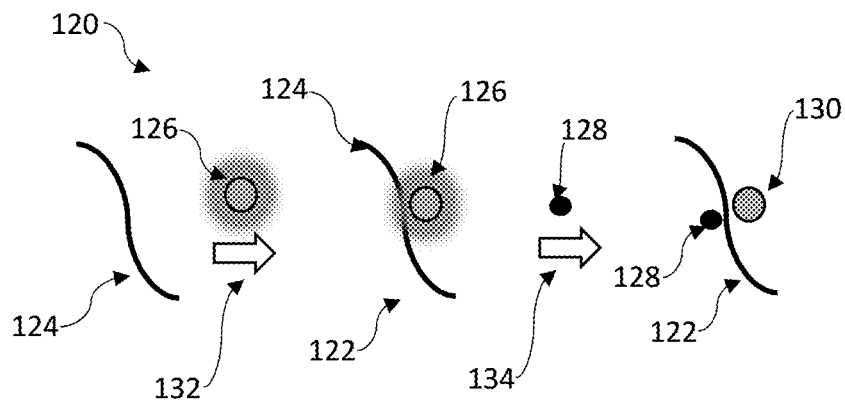
FIG. 1B depicts a schematic diagram of another fluorescence sensor, in accordance with the disclosed embodiments.

FIG. 1B illustrates another embodiment of a method 120 wherein the use of a different fluorophore allows facile tuning of the associated emission. Specifically, in FIG. 1B a red emitting fluorescence sensor 122 is illustrated, in accordance with the disclosed embodiments. The red emitting fluorescence sensor 122 uses a polymer 124 to non-covalently bind a red emitting fluorophore 126 and analyte 128. Again, the red emitting fluorescence sensor 122 is formed by binding the polymer 124 and red emitting fluorophore 126, as illustrated by arrow 132. It should be noted that, at this point the red emitting fluorophore 126 is fluorescing red, as illustrated by the halo surrounding fluorophore 126. The sensor 122 can then be introduced to an environment where the analyte 128 is suspected to be present. If the analyte 128 is present, the analyte 128 binds to the red emitting fluorescence sensor 122 as illustrated by arrow 134. The fluorescence "turns off," as illustrated by non-fluorescing fluorophore 130 which a skilled artisan will appreciate is the same structure as fluorophore 126), of sensor 122, indicating that the analyte 128 is present.

Figure 1C:
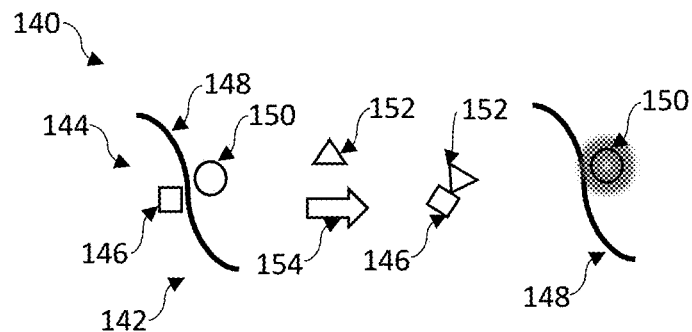
FIG. 1C depicts a schematic diagram of an "Off-On" fluorescence sensor, in accordance with the disclosed embodiments.

FIG. 1C illustrates another embodiment of a method 140 wherein an "Off-On" fluorescence sensor 142 is illustrated. The Off-On fluorescence sensor 142 is comprised of a non-fluorescent polymer-fluorophore-quencher complex 144 comprising a quencher 146 bound to a polymer 148 and a fluorophore 150. The analyte 152 has a higher affinity for the quencher 146 than the polymer 148. Thus, as shown by arrow 154 the analyte 152 displaces the quencher 146 from the non-fluorescent polymer-fluorophore-quencher complex 144, restoring fluorescence to the fluorophore 150 as shown by the halo, and enabling detection of the desired compound.

Figure 2A:
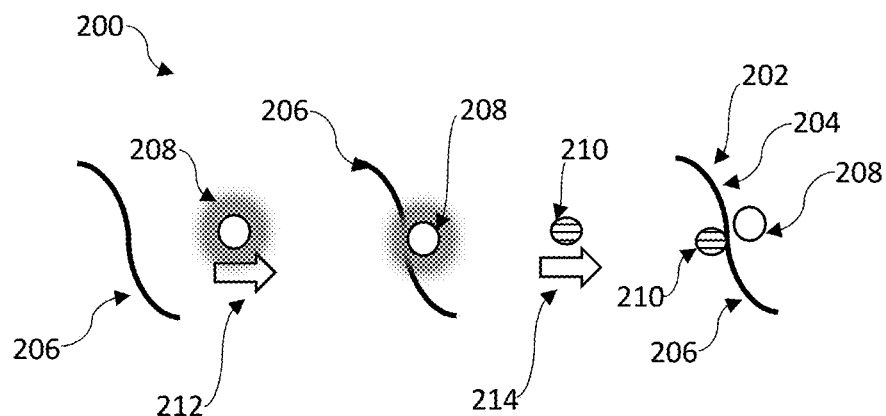
FIG. 2A depicts a schematic diagram of a sensor assembly, in accordance with the disclosed embodiments.
Figure 2B:
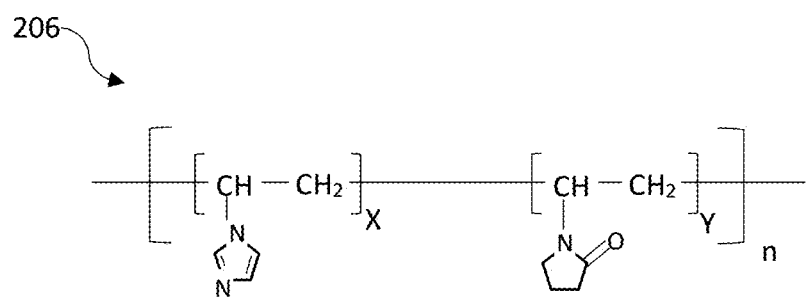
FIG. 2B depicts a chemical formula of a polymer used in a sensor, in accordance with the disclosed embodiments.

In certain embodiments, the disclosed sensors are non-covalent complexes of: a fluorophore (F), a polymer (P), and a quencher (Q) or "FPQ" complexes. FIG. 2 illustrates an assembly method 200 for an FPQ sensor 202 in accordance with an embodiment of the claimed sensors. As illustrated in FIG. 2A the assembled sensor 202 comprises a fluorophore-polymer-quencher complex 204.

As illustrated in FIG. 2A, polymers 206, which can comprise poly(N-vinylimidazole) (PVI) and/or poly(N-vinylimidazole-co-N-vinypyrrolidone) (P(VI-co-VP)) are required. A chemical representation of polymer 206 is provided in FIG. 2B. The polymer 206 can be used to bind and induce molecular contact between the signaling fluorophore 208 and quencher 210. The quencher 210 can comprise $Cu^{2+}$ or AuNP. As illustrated by arrow 212, the polymer 206 and fluorophore 208 bind. Fluorophore complexation with the polymer 206 is accompanied by a significant increase in brightness. As illustrated by arrow 214, the quencher 210 can then bind to form the complex 204.

The fluorophore-polymer as well as FPQ complex formation can be achieved with simple mixing of individual components in deionized water. The disclosed sensor assembly method 200 can therefore be based on mixing of fluorophore 208, polymer 206, and quencher 210, which can circumvent the need for difficult synthesis associated with certain prior art approaches.

In an exemplary embodiment, the sensor can be assembled using Homo and copolymers of N-vinylimidazole. PVI and P(VI-co-VP) are exemplary choices for use in the assembly of $CN^-$ sensors because these polymers bind both the fluorophore as well as the quencher (e.g., $Cu^{2+}$ and AuNPs). Furthermore, $CN^-$ sensor (non-fluorescent FPQ complexes) assembly requires the use of a polymer that binds both the fluorophore and the quencher. It should be appreciated that the quencher can be any agent that can quench fluorescence (including, but not limited to, ions and nanoparticles). The term "quenching" or "fluorescence quenching" as used herein refers to a decrease in fluorescence of the sensor in the presence of a quencher or analyte as compared to the fluorescence of the sensor in the absence of the quencher or analyte.

PVI possesses many imidazole groups with a pKa~6.0 and, therefore, can possess a negligible positive charge (polycations are cytotoxic) at physiological pH (pH ~7.4; PVI is not a polycation at this pH). Cell viability studies demonstrate that even at low levels/degrees of alkylation, the alkylated-PVIs (polycations) display negligible cytotoxicity. Given the non-toxic nature of the homopolymer of VP, co-polymerization of VI with VP does not compromise the benign toxicity profile of the PVI. PVI and P(VI-co-VP) are therefore good choices for use in the assembly of CN⁻ sensors due to their favorable toxicity profiles.

PVI and P(VI-co-VP) also enable production of highly water soluble sensors. The dye-transfer-inhibition (DTI) properties of P(VI-co-VP) ensure water solubility of the sensors (non-fluorescent FPQ complexes) because DTI's are designed to keep dyes in solution through the formation of highly water-soluble DTI-dye complexes.

Figure 3A:
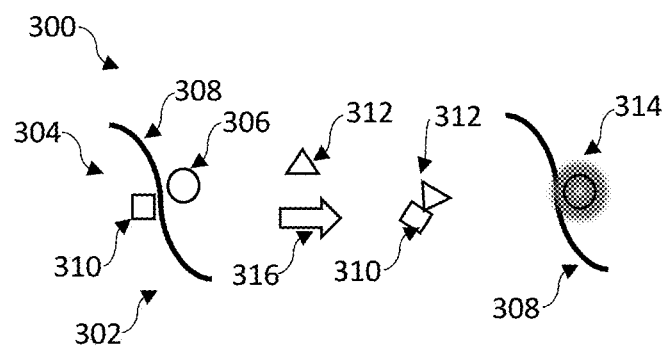
FIG. 3A depicts a schematic diagram of sensing mechanism when the quencher is $Cu^{2+}$, in accordance with the disclosed embodiments.

The CN⁻ sensing capability of an FPQ complex (with a CN⁻ sensor) comprising 0.13 µM (F), 0.37 µM (P), and 2 µM (Q) can be synthesized in deionized water. The addition of CN⁻ can restore or "turn-on" the fluorescence of the sensor. FIG. 3A illustrates the sensing process 300 for CN⁻ sensing when the quencher is $Cu^{2+}$. As illustrated in FIG. 3A the CN⁻ sensor 302 comprises a non-fluorescent fluorophore 306—polymer 308—quencher 310 complex 304. As illustrated by arrow 316 the presence of CN⁻ 312 displaces $Cu^{2+}$ quencher 310 from the complex 304, and the fluorescence is "switched on" as illustrated by fluorescing fluorophore 314 (which a skilled artisan will appreciate is the same structure as fluorophore 306).

The sensor 302 can be used to quantitatively detect CN⁻ levels as low as 15 µM. At ~15 µMCN⁻, fluorescence recovery is visually discernible. The term "restored" or "turned-on" as used herein refers to an increase in fluorescence of a sensor in the presence of analyte as compared to the fluorescence of a sensor in the absence of analyte. The CN⁻ detection limit of the FPQ complex 304 is approximately 10 µM, and is also well below the 300-500 µM levels produced by cyanogenic bacterial cultures grown under hypoxic conditions. One of the uses on the cyanide sensor 302 can therefore be for early detection of cyanogenic bacterial infections in burn wounds as well as the lungs of cystic fibrosis patients.

In certain embodiments, mechanisms of potential interference may be present and remedial strategies can be implemented. For example, CN⁻ displaces $Cu^{2+}$ from the sensor and produces the "turn-on" fluorescent signal. The displacement occurs because $Cu^{2+}$-cyanide affinity is greater than $Cu^{2+}$-polymer affinity. Sulfide[19] and iodide[24] anions as well as siderophores secreted by microorganisms also have high affinity for $Cu^{2+}$. These species can also displace $Cu^{2+}$ from the sensor and produce a false "turn-on" signal. In case false positives are observed, $Cu^{2+}$-polymer binding strength can be increased by using PVI instead of P(VI-co-VP) in the fluorophore-polymer-$Cu^{2+}$ complex. The increased $Cu^{2+}$-polymer affinity will make it impossible for the aforementioned species to displace copper, thus eliminating interference. $Cu^{2+}$-polymer binding strength in VI-containing polymers depends on the number of imidazole ligands that complex with the same $Cu^{2+}$ ion. Increasing VI mole fraction in P(VI-co-VP) copolymers can increase $Cu^{2+}$-polymer binding strength.

Figure 3B:
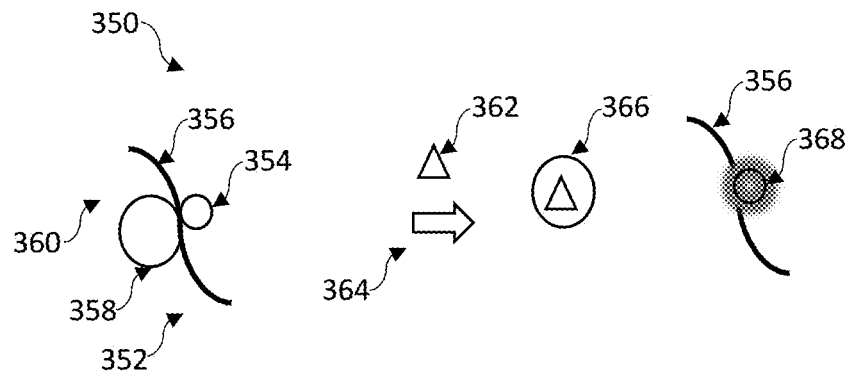
FIG. 3B depicts a schematic diagram of sensing mechanism when the quencher is gold nanoparticle, in accordance with the disclosed embodiments.

Gold nanoparticles (AuNPs) can be used in place of $Cu^{2+}$ in the fluorophore-polymer-quencher complex to overcome $S^{2-}$, $I^-$ and siderophore interference, as illustrated in FIG. 3B. AuNPs are efficient fluorescence quenchers and imidazole-functionalized polymers are known to bind AuNPs. The process 350 illustrated in FIG. 3B makes use of a CN⁻ sensor 352. The sensor 352 can comprise a non-fluorescent fluorophore 354—polymer 356—quencher 358 complex 360. In the presence of CN⁻ 362, illustrated by arrow 364, the CN⁻ dissolves the AuNP quencher shown by 366 in the complex 360 and the fluorescence of the fluorophore 368 (which a skilled artisan will appreciate is the same structure as fluorophore 354) is "switched on."

The advantage of assembling sensors in which AuNPs are the quenchers is that "turn-on" detection of CN⁻ occurs via dissolution of AuNPs as shown in FIG. 3B, which, under physiological conditions, is highly specific to CN⁻. The use of AuNPs as quenchers also illustrates that the mechanism of quencher removal can vary. The term "remove," "removing," and "removal" as used herein with respect to the quencher refers to any mechanism or process that results in the quencher no longer being able to quench the fluorescence of the FPQ complex.

The disclosed sensor produces a greatly enhanced "turn-on" signal because the fluorescing species in the sensor is a fluorophore-polymer complex rather than free fluorophore. Fluorophore-polymer complexes can display a much stronger fluorescent signal than the un-complexed fluorophore. In certain embodiments, sensor assembly can be achieved using longer wavelength fluorophores. Applications involving tissue or blood, for example, require sensors comprising far-red or near-infrared fluorophores to overcome tissue auto fluorescence and absorption from hemoglobin.

Figure 4A:
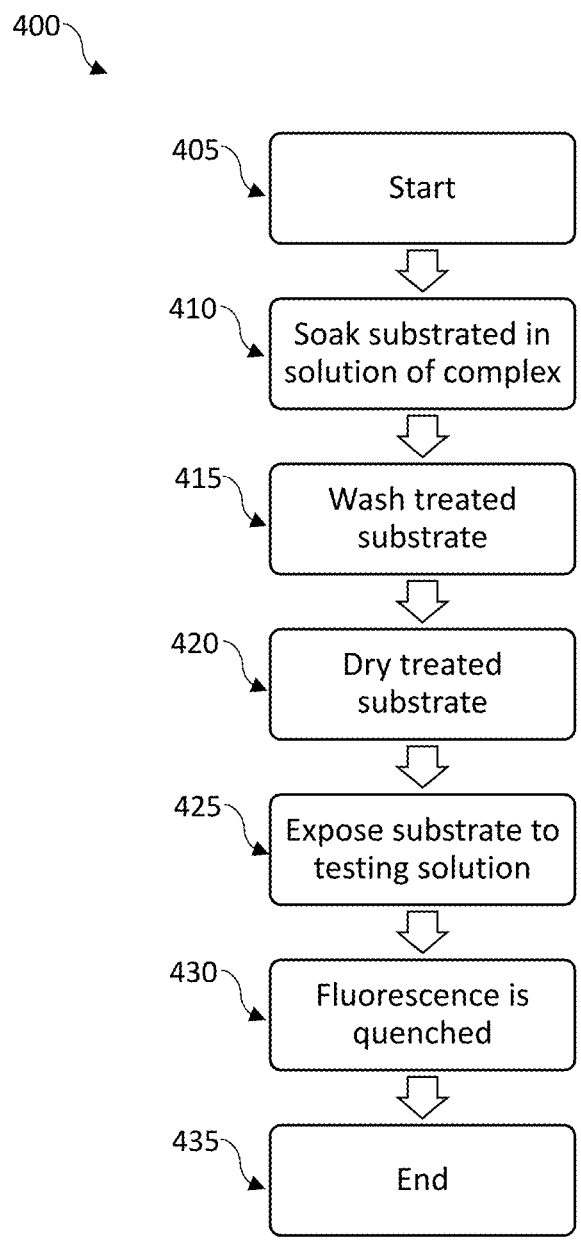
FIG. 4A depicts steps associated with a sensing method, in accordance with the disclosed embodiments.
Figure 4B:
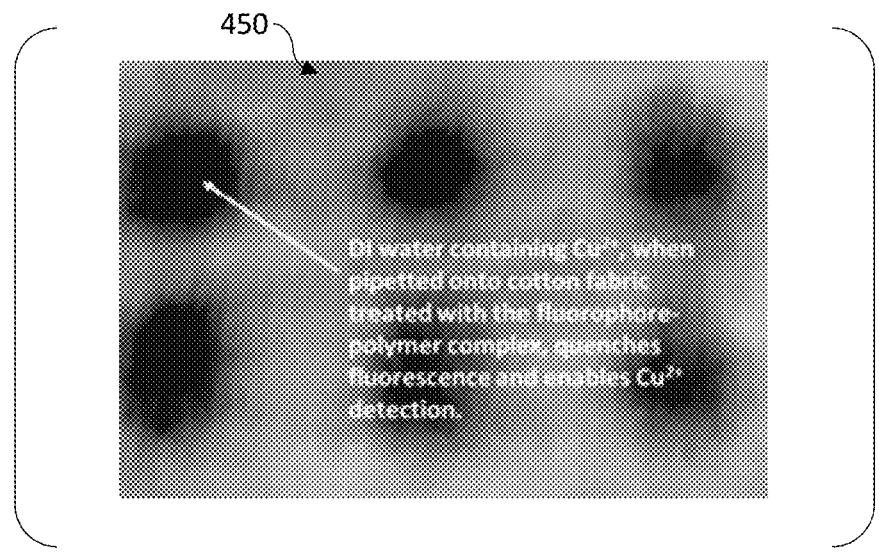
FIG. 4B depicts a photograph of a "dip-in" sensor, in accordance with the disclosed embodiments.
Figure 4C:
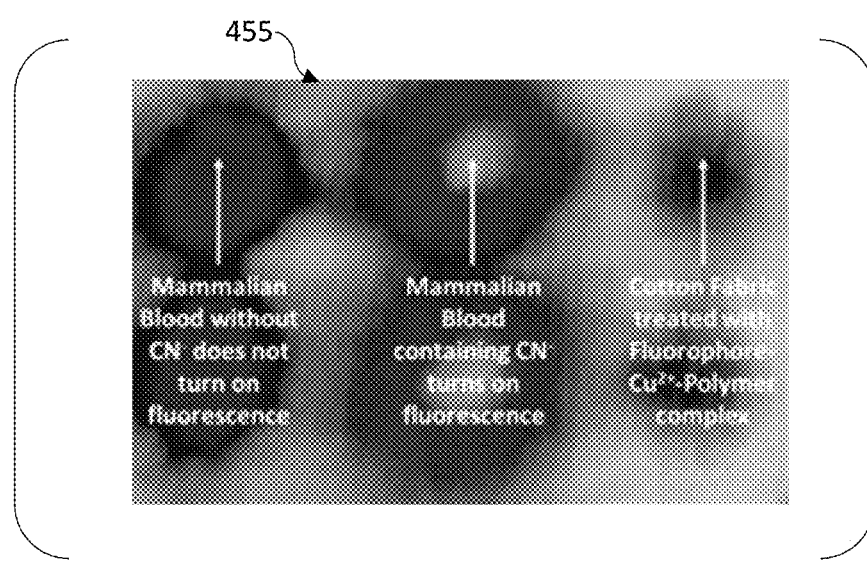
FIG. 4C depicts a photograph of another "dip-in" sensor, in accordance with the disclosed embodiments.

According to the disclosed methods and systems, the disclosed sensors can be incorporated onto a solid substrate as illustrated in FIG. 4A. For example, the disclosed sensors can be incorporated onto solid substrates, according to the method 400, to make "dip-in" sensors for a variety of analytes. The method begins at 405. Next, to prepare such "dip-in" sensors, the solid substrate (e.g., cotton, fabric, nylon, polyester, paper-based, etc.) is soaked in a solution of the fluorophore-polymer complex as shown at 410. The treated substrate can be washed at step 415 and dried at step 420. When a drop of solution containing $Cu^{2+}$ is pipetted onto the substrate as shown at 425, the fluorescence of the spotted area is quenched as illustrated by 430, thereby enabling analyte detection. The method ends at 435. FIG. 4B illustrates a photograph of a dip-in sensor 450, used to detect $Cu^{2+}$. The substrate can also be used to detect CN⁻ levels in whole blood as illustrated by the photograph of a dip-in sensor 455 in FIG. 4C.

Thus, the sensors can be easily used to prepare dip-in sensors for facile, rapid detection of target analytes in the field (e.g., monitoring of water quality or rapid diagnosis of cyanide poisoning in fire-victims and fire-fighters) as well as at the bedside (e.g., indirect monitoring of bacterial infection), and for disease diagnosis in remote areas (e.g., detection of certain enzymes in urine as a cancer marker). As noted above, cotton or other such materials, stained with fluorophore-polymer complexes can be used as sensitive, practical, in-field dip-in sensors for $Cu^+/Cu^{2+}$.

Figure 5:
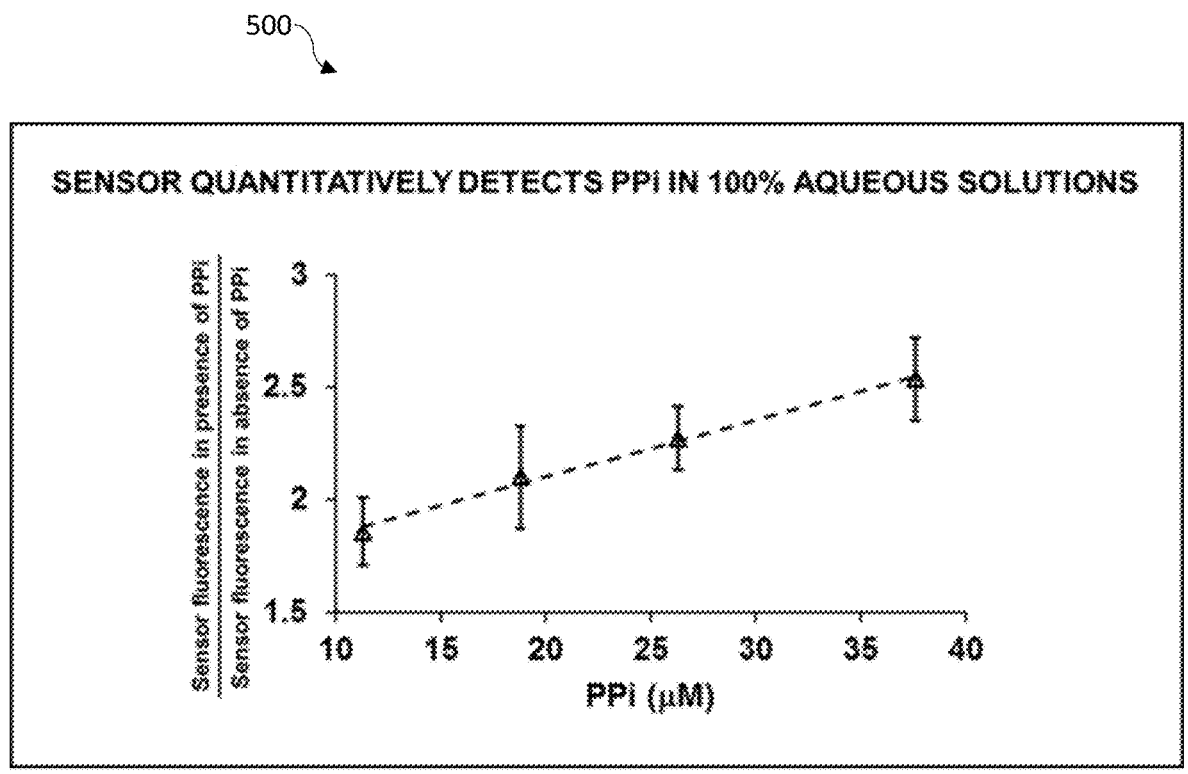
FIG. 5 depicts a chart illustrating sensor fluorescence as a function of PPi level, in accordance with the disclosed embodiments.

In another embodiment, the sensor (FPQ complex) can quantitatively detect pyrophosphate (PPi) in 100% aqueous solutions. FIG. 5 provides a chart 500 that illustrates that sensor fluorescence increases as the presence of PPi increases in aqueous solutions. Likewise, in embodiments, the sensor can detect enzyme activity in aqueous media. For example, the sensor (fluorophore-polymer-$Cu^{2+}$) can detect trypsin activity in aqueous media.

Figure 6A:
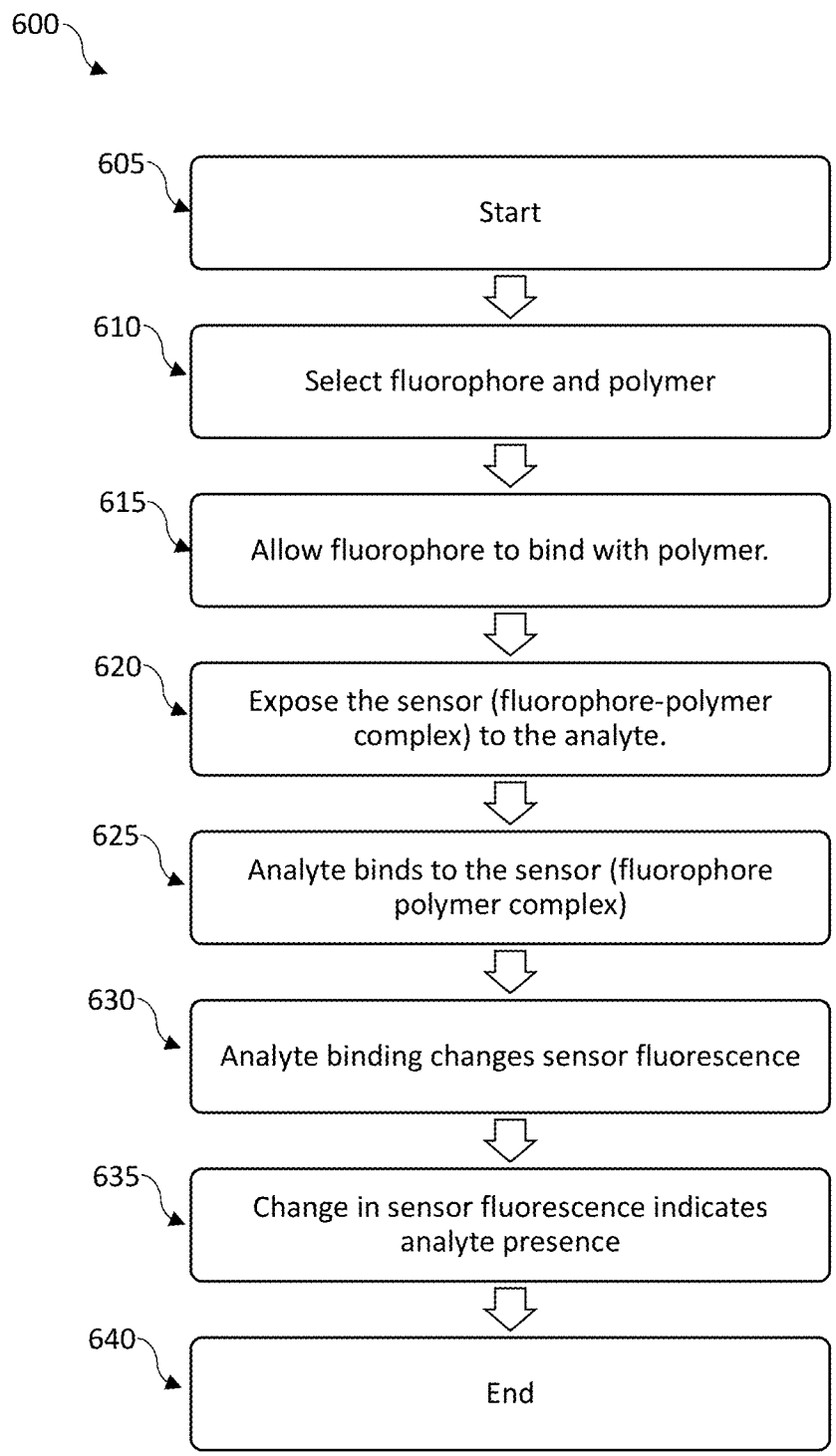
FIG. 6A depicts steps associated with a sensing method, in accordance with the disclosed embodiments.

An exemplary method 600 illustrated in FIG. 6A. The method begins at 605 after which, a commercially available, as-received fluorophore, and polymer are selected at step 610. At step 615, the fluorophore is allowed to bind with the polymer, which can result in a significant increase in fluorescence of the complex. This fluorophore-polymer complex is one kind of sensor described herein.

The sensor is then exposed to the testing environment, which may have the analyte therein, as shown at 620. As illustrated at 625, the polymer binds the analyte if it is present. Molecular contact between the analyte and complex is achieved, inducing a change in fluorescence as shown at 630. The change in fluorescence is indicative of the presence of the analyte as shown at 635. The method ends at 640.

Figure 6B:
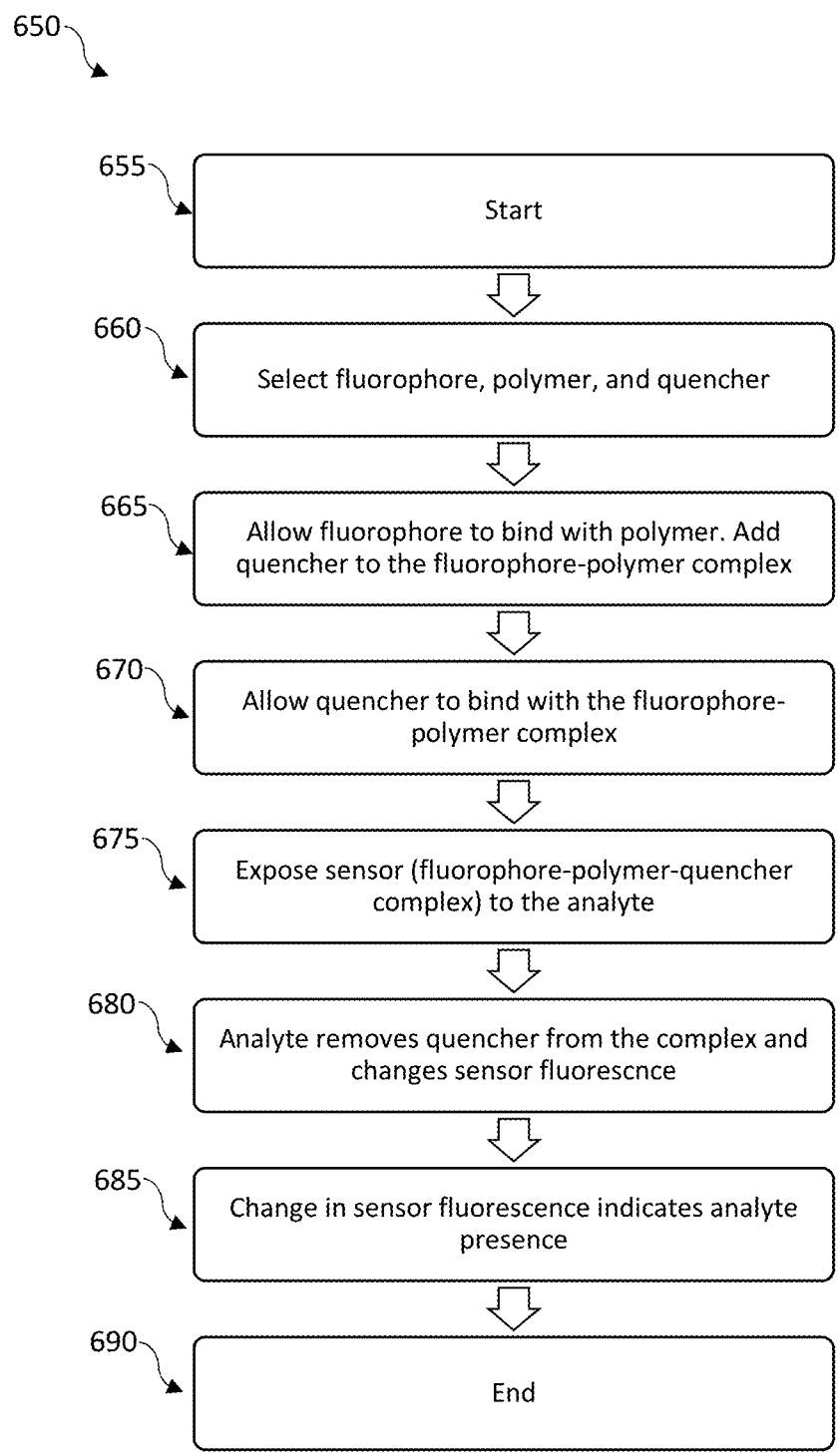
FIG. 6B depicts steps associated with another sensing method, in accordance with the disclosed embodiments.

Another exemplary method 650 is illustrated in FIG. 6B. The method 600 begins at 655. Next, a commercially available, as-received fluorophore, polymer, and quencher are selected at 660. The fluorophore is allowed to bind with the polymer, which can result in a significant increase in fluorescence. The fluorophore-polymer complex is then mixed with a quencher at step 665, and the quencher can then bind with the fluorophore-polymer complex at step 670 to form a fluorophore-polymer-quencher complex. This is another type of sensor disclosed herein.

The sensor is then exposed to a substance or environment where the analyte may be present at step 675. In the presence of an analyte, the analyte can remove the quencher at step 680. Removal of the quencher causes a change in fluorescence as illustrated at 685, which is indicative of the presence of the analyte. The method ends at 690.

It should be understood that, in other embodiments, the sensor can be configured in other ways. For example, in an embodiment, the sensor can be a non-covalent complex of two or more commercially available, as-received fluorophores, and a metal ion binding polymer. Upon exposure to a metal ion, the fluorescence of at least one of the fluorophores in the non-covalent complex is quenched resulting in a change in fluorescence.

In another embodiment, the sensor comprises a mixture of a non-covalent complex of at least one commercially available, as-received fluorophore, and a metal ion binding polymer and at least one free/unbound/un-complexed fluorophore. Upon exposure to a metal ion, the fluorescence of at least one of the fluorophores in the non-covalent complex is quenched resulting in a change in fluorescence.

In another embodiment, the sensor can be a non-covalent complex of two or more commercially available, as-received fluorophores, a polymer, and a quencher, wherein the fluorescence of at least one of the fluorophores in the non-covalent complex is quenched by the quencher. Upon exposure to an analyte that can remove the quencher, a change in fluorescence is observed. The change in fluorescence is indicative of the presence of the analyte.

In another embodiment, the sensor comprises a mixture of a non-covalent complex of at least one commercially available, as-received fluorophore, a metal ion binding polymer, and a quencher; and at least one free/unbound/un-complexed fluorophore. Upon exposure to an analyte that can remove the quencher, a change in fluorescence is observed.

Figure 7:
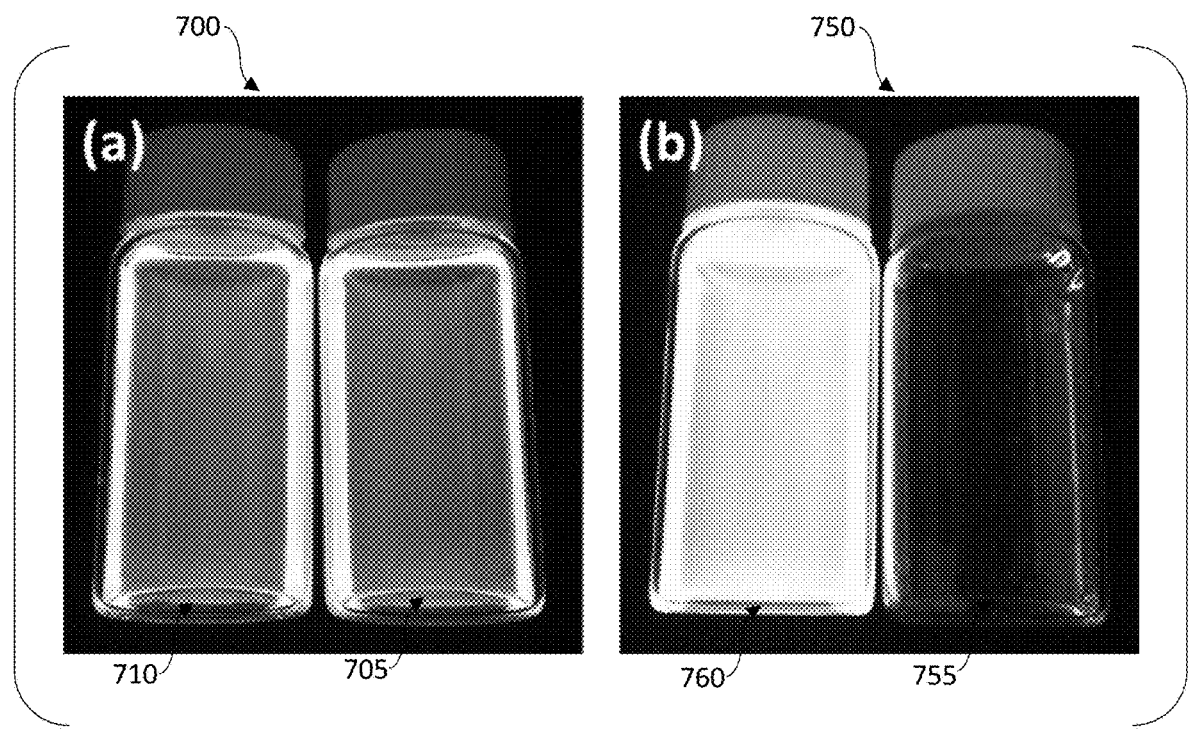
FIG. 7 depicts a photograph of a sensor applied to a solution, in accordance with the disclosed embodiments.

FIG. 7 provides two side by side photographs 700 and 750 of UV-Illuminated, aqueous solutions in accordance with the disclosed embodiments. The solution in photograph 700 comprises a quantity of diaminostilbene fluorophore (e.g., 10 ppm) and PVP (e.g., 100 ppm). In photograph 700 the right bottle 705 has $Cu^{2+}$ and the left bottle 710 does not have $Cu^{2+}$. As illustrated by the photograph 700, PVP cannot bind copper and, as a result, detection of $Cu^{2+}$ is impossible.

In photograph 750, the aqueous solution contains a quantity of diaminostilbene fluorophore (e.g., 10 ppm) and P(VP-co-VI) (e.g., 100 ppm). In photograph 750 the right bottle 755 has $Cu^{2+}$ and the left bottle 760 does not have $Cu^{2+}$. In photograph 750, the imidazole groups in P(VP-co-VI) bind with the copper enabling successful detection of $Cu^{2+}$ in the 100% aqueous medium.

FIG. 7 illustrates a key to the disclosed sensors—namely the polymer has a high affinity for both fluorophore as well as analyte. Fluorophore binds to both polymers (PVP and P(VP-co-VI)) used in the solution illustrated in photograph 700. However, the PVP-fluorophore complex cannot detect $Cu^+/Cu^{2+}$ because PVP cannot bind copper ions. The P(VP-co-VI)-fluorophore complex, as shown in photograph 750 on the other hand, is an excellent $Cu^+/Cu^{2+}$ sensor because of the affinity of the imidazole groups for copper.

Suitable polymers for use in the disclosed sensors include commercially available dye-transfer-inhibitors. A dye transfer inhibitor is designed to capture or bind and solubilize dyes that become detached. As a result, in addition to circumventing complicated synthesis and increasing probe brightness, the disclosed sensors also enhance probe water solubility.

Another advantage of the proposed approach is that, since there are no covalent bonds between polymer, fluorophore, and analyte, several different fluorophores can be used with the same polymer as illustrated, for example, in FIG. 1B. Thus, a blue fluorescent sensor assembled for environmental monitoring of $Cu^{2+}$, as shown in FIG. 1A, can be adapted for biosensing of the same ion in live cells and tissues, where autofluorescence necessitates longer wavelength probes, by simply switching out the blue fluorophore for a red or NIR emitter as shown in FIG. 1B.

Anion sensing via the displacement approach disclosed herein can be used for assembly of luminescent probes for use in vitro and in vivo bioimaging and biological applications. The displacement approach can also be used to develop fluorescence assays for enzyme and enzyme activity detection and drug discovery. As shown schematically in FIG. 1C, the embodiments disclosed herein can provide facile assembly of fluorescent probes for analyte sensing via the displacement approach, without the drawbacks faced by current fluorescence sensors.

In another embodiment, a luminol-$Cu^{2+}$-PVI or P(VI-co-VP) complex for enhanced chemiluminescent detection of $H_2O_2$ in weakly acidic, neutral, and alkaline media is disclosed. Luminol, PVI/P(VI-co-VP), $H_2O_2$ mixtures can be used to assemble highly sensitive and specific "Off-On" sensors for $Cu^{2+}$. Because the appearance of a bright signal on a completely dark background is easier to detect than the dimming of an already bright signal, the "Turn-On" chemiluminescent $Cu^{2+}$ sensors can outperform the "Turn-Off" fluorescent $Cu^{2+}$ sensors. The disclosed Chemiluminescence-based methods and systems can be used in clinical diagnostics, analysis, and research as well as environmental monitoring due to their high sensitivity, specificity, low limit of detection, wide operating range, and convenience.

In an embodiment, Fluorophore-PVI or fluorophore-P(VI-co-VP) complexes can be used to detect $Cu^{\pm}/Cu^{2+}$ and $Hg^{2+}$ in 100% aqueous systems with high sensitivity and specificity. Fluorophore-PVI or fluorophore-P(VI-co-VP) ratios that maximize sensitivity towards cationic analytes such as $Cu^{2+}$ and $Hg^{2+}$ can be selected. Interference due to other metal ions can also be considered. Fluorophore-PVI-$Cu^{2+}$ complexes can be used in combination with diethyldithiocarbamate (DDTC) to sense $Hg^{2+}$. Sensitive, practical, in-field dip-in sensors for $Cu^+/Cu^{2+}$ can be provided using cotton (or other such base substrates), stained with either fluorophore-PVI or fluorophore-P(VI-co-VP) complexes.

Fluorophore-PVI or P(VI-co-VP) -$Cu^{2+}$ complexes can be used in combination with diethyldithiocarbamate (DDTC) to sense $Hg^{2+}$. DDTC can chelate and remove $Cu^{2+}$ from the non-fluorescent fluorophore-PVI-$Cu^{2+}$ complex, producing a fluorescent (turn-on) and colorimetric (DDTC-$Cu^{2+}$ complex is yellow with maximum absorbance at ~450 nm) response. $Hg^{2+}$ will displace $Cu^{2+}$ from the DDTC-$Cu^{2+}$ complex, causing an inverse fluorescence (turn-off) and colorimetric (DDTC-$Hg^{2+}$ complex shows no appreciable absorbance from 400 nm-800 nm) response. Absorbance characteristics of the DDTC-$Cu^{2+}$ necessitate the use of fluorophores that show minimal absorbance below 500 nm and emit in the 600-800 nm range (e.g., Rhodamine B or 6G). The presence of interfering species such as other metal ions may affect the sensitivity and selectivity of $Hg^{2+}$ detection disclosed herein.

In another embodiment, "Turn-On" fluorescent sensors for $CN^-$, $I^-$, PPi, and $H_2S/HS^-/S^{2-}$ are disclosed. Non-fluorescent PVI-$Cu^{2+}$-fluorophore and P(VI-co-VP)-$Cu^{2+}$-fluorophore complexes can be used. For example, analyte-induced displacement of $Cu^{2+}$ from these complexes is shown in FIG. 1C. Specific sensing of each anion mentioned above is possible, provided the strength of the polymer-$Cu^{2+}$ interaction is tuned to be comparable to the affinity between $Cu^{2+}$ and the anion of interest. This can be achieved by using (a) P(VI-co-VP) polymers with different mole fractions of N-vinylpyrrolidone to weaken $Cu^{2+}$-polymer affinity and (b) homo and copolymers of polymer bound iminodiacetate-type chelating agents to obtain higher $Cu^{2+}$-polymer affinity.

It should be appreciated that the binding of a single imidazole ligand to $Cu^{2+}$ is much weaker (log K=3.76) than the binding of $Cu^{2+}$ to PVI (log K~12.6). The strength of the interaction between $Cu^{2+}$ and PVI stems from the ability of four imidazole ligands to form a complex with the same $Cu^{2+}$ ion. Copolymerization with N-vinylpyrrolidone reduces the number of imidazole ligands that can complex with a single $Cu^{2+}$ ion, thereby decreasing $Cu^{2+}$-polymer interaction strength. Each anion mentioned above can displace $Cu^{2+}$ from the non-fluorescent complexes of $Cu^{2+}$, fluorophore, and P(VI-co-VP) polymers with mole fractions of N-vinylpyrrolidone ranging from 0 to 0.9.

Transition metal ions like $Cu^{2+}$ bind to iminodiacetic acid (IDA) with such strength that they are used in immobilized metal affinity chromatography (IMAC) to fractionate protein solutions. $Cu^{2+}$ may have higher affinity for polymers containing covalently bound iminodiacetate groups than for PVI. Homo and copolymers of vinylbenzylamine-N,N-diacetic acid and N-vinylpyrrolidone and homo and copolymers of glycidyl methacrylate-iminodiacetic acid are two suitable examples. Each anion mentioned above can displace $Cu^{2+}$ from the non-fluorescent $Cu^{2+}$-fluorophore-polymer complexes.

Accordingly, the fluorophore significantly affects the nature of the interactions in the disclosed systems. Upon complexation with an ionic fluorophore, both PVI and P(VI-co-VP) can become charged macromolecules, adopting a more expanded-coil configuration. Electrostatic repulsion between adsorbed fluorophores may have a significant impact on strength of $Cu^{2+}$ binding to PVI or P(VI-co-VP), and consequently, the sensitivity and specificity of anion detection. Non-fluorescent PVI-$Cu^{2+}$-fluorophore and P(VI-co-VP)-$Cu^{2+}$-fluorophore complexes can be used to detect $CN^-$, $I^-$, PPi, and $H_2S/HS^-/S_2$ via anion-induced displacement of $Cu^{2+}$ from these complexes. $Cu^{2+}$-polymer affinity can be tuned to achieve specific sensing of each anion, including: P(VI-co-VP) polymers with different mole fractions of N-vinylpyrrolidone to weaken $Cu^{2+}$-polymer affinity; and homo and copolymers of polymer bound iminodiacetate-type chelating agents to obtain higher $Cu^{2+}$-polymer affinity. Finally, the effect of bound fluorophore on strength of $Cu^{2+}$ binding to polymer, and consequently, the sensitivity and specificity of anion detection should be considered.

In another embodiment, a "Turn-Off" and "Turn-On" sensor for enzyme activity is disclosed. In certain embodiments, detection of protease activity can use bovine serum albumin (BSA) as a substrate and trypsin as the protease enzyme. One skilled in the art should appreciate that in other embodiments detection can be accomplished using different substrates and enzymes without departing from the disclosure provided herein.

Figure 8:
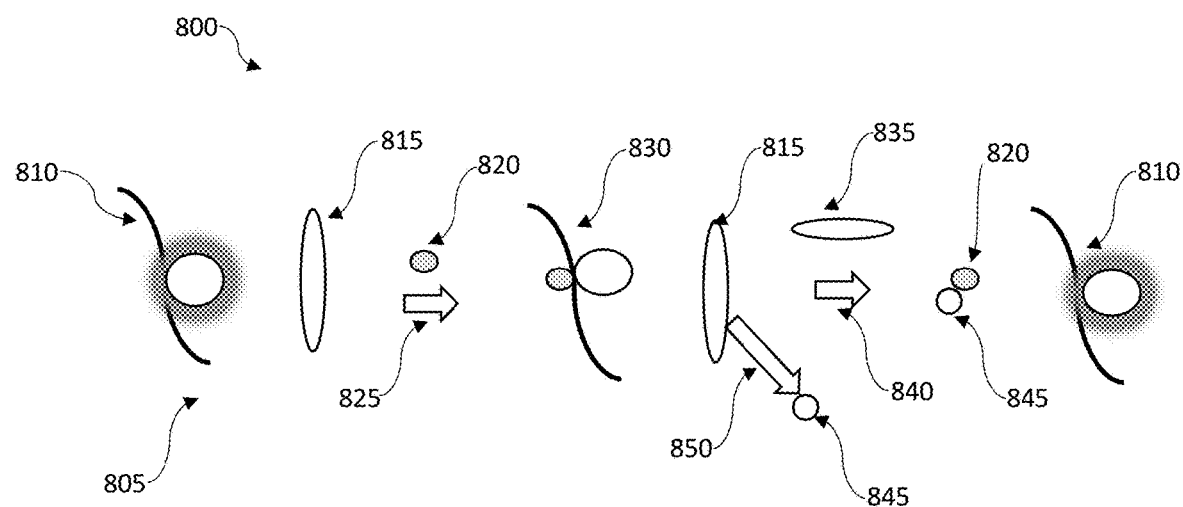
FIG. 8 depicts a schematic diagram of a sensor for the detection of a protease, in accordance with the disclosed embodiments.

FIG. 8 illustrates a method 800 associated with a sensor 805 in accordance with the disclosed embodiments. The solution can initially contain a fluorophore-PVI or P(VI-co-VP) complex 810 and protein 815 as the protease substrate. When $Cu^{2+}$ 820 is added to this mixture, as shown by arrow 825, the fluorescence may be quenched due to formation of a fluorophore-polymer-Cu2+ complex 830. Addition of protease 835, as shown by arrow 840, will cause the substrate protein to be cleaved, as shown by arrow 850, into amino acid and peptide fragments 845 which, because of their strong affinity for $Cu^{2+}$, will displace the copper ions 820 from non-fluorescent fluorophore-polymer-$Cu^{2+}$ complex, restoring fluorescence.

Figure 9:
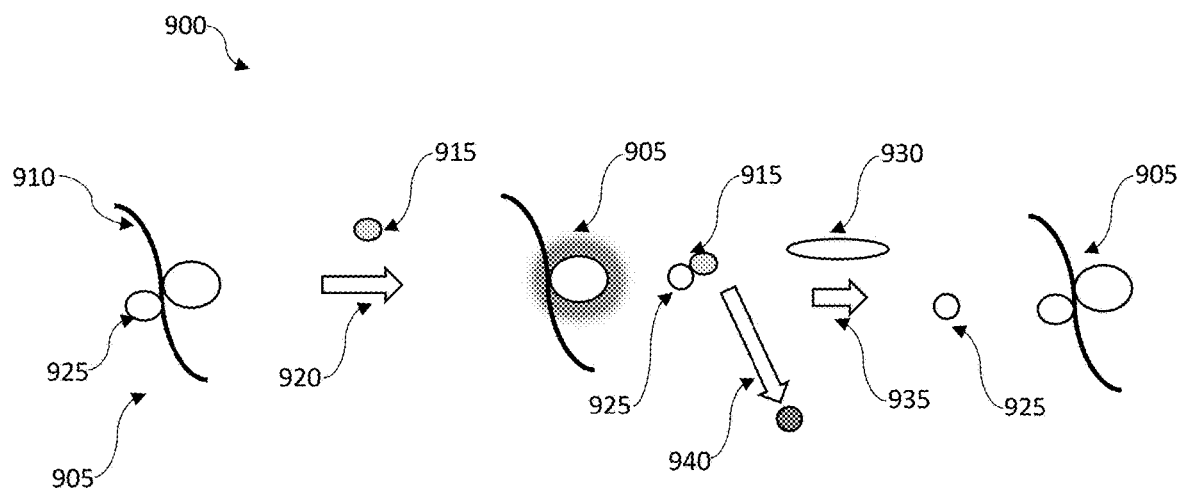
FIG. 9 depicts a schematic diagram of a sensor for the detection of a phosphatase, in accordance with the disclosed embodiments.

Detection of phosphatase activity can use PPi as a substrate and alkaline phosphatase (ALP) as the phosphatase enzyme. An associated method 900 is illustrated in FIG. 9, in accordance with the disclosed embodiments. The solution initially contains a sensor 910 comprising a non-fluorescent fluorophore-polymer-$Cu^{2+}$ complex 905. When PPi 915 is added to this mixture, as shown by arrow 920, it can displace the copper ions 925 from non-fluorescent fluorophore-polymer-$Cu^{2+}$ complex 905, restoring fluorescence. The addition of ALP 930, as shown by arrow 935 addition will initiate PPi hydrolysis, as illustrated by arrow 940, releasing $Cu^{2+}$ 925 which, in turn, will bind to the fluorophore-polymer complex 905 and quench fluorescence.

Other embodiments of such sensors are also possible. For example, detection of kinase activity can use adenosine-5'-triphosphate (ATP) as a substrate for enzyme adenylate kinase (ADK). ATP can displace $Cu^{2+}$ from the non-fluorescent fluorophore-polymer-$Cu^{2+}$ complex. ADK catalyzes conversion of ATP to ADP, releasing $Cu^{2+}$ which, in turn, will bind to the fluorophore-polymer complex and quench fluorescence.

It should be appreciated that the disclosed methods and systems can yield equivalent sensitivity from the fluorophore-PVI or P(VI-co-VP)-$Cu^{2+}$ system, to prior art methods, with the benefit of facile tuning of probe emission tuning, enhanced water solubility, and brightness and circumvention of synthesis steps.

Thus, according to the above embodiments, a non-fluorescent polymer-c-fluorophore complex can be used to detect protease activity using bovine serum albumin (BSA) as a substrate and trypsin as the protease enzyme. A non-fluorescent PVI-$Cu^{2+}$-fluorophore complex can be used to detect phosphatase activity using pyrophosphate (PPi) as substrate and alkaline phosphatase (ALP) as phosphatase enzyme. Non-fluorescent PVI- $Cu^{2+}$-fluorophore complex can be used to detect kinase activity using adenosine-5'-triphosphate (ATP) as substrate for enzyme adenylate kinase (ADK).

In yet another embodiment, chemiluminescence sensors for $Cu^{2+}$ and $H_2O_2$ are disclosed. $Fe^{3+}$, $Co^{2+}$, and $Cu^{2+}$ and their complexes are stable, efficient, inexpensive enhancers for the $H_2O_2$-luminol light-emitting reaction. Binding of luminol to water soluble polymers can provide significant chemiluminescence enhancement.

In the disclosed embodiments, chemiluminescent signals from the $H_2O_2$-luminol-$Cu^{2+}$ system in the presence of (a) PVP, a polymer that can only bind luminol and (b) PVI, one that can bind both metal ion and luminol can be compared.

The disclosed embodiments can thus be used to assemble more sensitive chemiluminescent probes for environmental and clinical applications.

In certain embodiments, facile assembly of sensors for $H_2O_2$ are disclosed, that work in alkaline, neutral, and weakly acidic media by using complexes of homo and co-polymers of N-vinyl imidazole with luminol and $Cu^{2+}$. These sensors provide rapid, inexpensive, in-field testing of aquatic media such as rain and seawater. The disclosed diagnostic tools can be used for the detection of substrates of enzymes releasing $H_2O_2$ (e.g., glucose and cholesterol). To accomplish this, first it is necessary to measure chemiluminescent signals obtained upon addition of $H_2O_2$ to (a) the PVI-luminol-$Cu^{2+}$ complex, (b) luminol only, and (c) mixtures of luminol and $Cu^{2+}$. The effect of pH on the PVI-luminol-$Cu^{2+}$ chemiluminescent signal can also be considered. The PVI-luminol-$Cu^{2+}$ complex shows the greatest chemiluminescence enhancement and consequently the highest $H_2O_2$ sensitivity in both mildly acidic/neutral as well as basic conditions.

Chemiluminescence signal enhancement can depend on a polymer/$Cu^{2+}$ ratio, with unsaturated $Cu^{2+}$-ligand complexes displaying greater catalytic enhancement. Two routes can be pursued to maximize sensitivity towards $H_2O_2$: 1) varying PVI/$Cu^{2+}$ ratios and 2) varying the mole fraction of N-vinylpyrrolidone in P(VI-co-VP) copolymers to control the proportion of unsaturated $Cu^{2+}$-ligand complexes at a given polymer/$Cu^{2+}$ ratio. Accordingly, the sensors disclosed herein can comprise PVI/P(VI-co-VP)-luminol-$Cu^{2+}$ sensors for the detection of $H_2O_2$ in mildly acidic, neutral, and alkaline media.

For environmental, clinical and biochemical analyses, determination of $H_2O_2$ and glucose in neutral or unbuffered solutions is desirable. In an embodiment, a glucose sensor based on glucose oxidase-catalyzed the oxidation of glucose to gluconic acid and $H_2O_2$ at pH ~5.8. The PVI/P(VI-co-VP)-luminol-$Cu^{2+}$ system can be used to detect and monitor the released $H_2O_2$ in these mildly acidic conditions.

In a further embodiment, a "Turn-On" sensor for $Cu^{2+}$ using $H_2O_2$ in combination with luminol-PVI/P(VI-co-VP) complexes is disclosed. Because the appearance of a bright signal on a completely dark background is easier to detect than the dimming of an already bright signal, the "Turn-On" chemiluminescent $Cu^{2+}$ sensors outperform the "Turn-Off" fluorescent $Cu^{2+}$ sensors outlined in other embodiments.

Thus, in certain embodiments, the synergistic effects of binding metal ion and luminol to the same polymer can be used to compare chemiluminescent signals from the $H_2O_2$-luminol-$Cu^{2+}$ system in the presence of (a) PVP, a polymer that can only bind luminol and (b) PVI, one that can bind both metal ion and luminol. The effect of pH on chemiluminescent signals from PVI-luminol-$Cu^{2+}$ complex in the presence of $H_2O_2$ can be considered. Proportion of unsaturated $Cu^{2+}$-ligand complexes can be controlled by varying PVI/$Cu^{2+}$ ratios and by varying the mole fraction of N-vinylpyrrolidone in P(VI-co-VP) copolymers to maximize catalytic chemiluminescence signal enhancement. PVI/P(VI-co-VP)-luminol -$Cu^{2+}$ sensors for the detection of $H_2O_2$ in mildly acidic, neutral, and alkaline media are disclosed that can be used to detect and monitor $H_2O_2$ released by glucose oxidase-catalyzed the oxidation of glucose at pH ~5.8. Luminol-PVI/P(VI-co-VP) complex can be used for chemiluminescent detection of $Cu^{2+}$.

In summary, the use of a polymer to non-covalently bind both signaling fluorophore and analyte as disclosed herein, is novel. Also, the use of non-covalent complexes of fluorophore, polymer, and quencher for analyte detection as disclosed herein, is novel. Similarly, synergistic effects of binding both metal ion and luminol to the same polymer is disclosed. The disclosed methods and systems address how PVI "concentrates" fluorophore and analyte, by focusing on fluorophore-PVI ratios that maximize sensitivity towards cationic analytes such as $Cu^{2+}$ and $Hg^{2+}$. Copolymers of N-vinylimidazole and N-vinylpyrrolidone can be used to vary the strength of the $Cu^{2+}$- polymer ligand interaction to control sensitivity and selectivity of anion sensing via $Cu^{2+}$ displacement, enable sensitive and specific detection of enzyme activity, and to systematically tune metal ion catalytic activity in the luminol- $H_2O_2$ chemiluminescence reaction. When applied to other $Cu^{2+}$-complexing polymer ligands such as polypeptides, polycarboxylic acids, poly(4-vinylpridine), and others, the disclosed systems and methods greatly expand the scope of sensing strategy with applications in clinical diagnostics and environmental and bioprocess monitoring.

Based on the foregoing, it can be appreciated that a number of embodiments, preferred and alternative, are disclosed herein. For example, in an embodiment a sensing method comprises assembling a sensor comprising at least one polymer and at least one fluorophore by mixing the polymer with the fluorophore, exposing the sensor to an analyte, and identifying the presence of the analyte according to a change in fluorescence of the sensor.

In an embodiment, the sensor comprises a non-covalent complex of the at least one fluorophore and the at least one polymer. In an embodiment, the at least one polymer comprises a polymer capable of binding a metal ion. In an embodiment, the at least one polymer capable of binding a metal ion comprises an imidazole-containing polymer. In an embodiment, the at least one polymer comprises at least one of an N-vinylimidazole homo polymer and/or an N-vinylimidazole co-polymer.

In an embodiment, assembling the sensor comprising at least one polymer and the at least one fluorophore by mixing the polymer with the fluorophore further comprises quenching fluorescence of the at least one fluorophore with at least one fluorescence quencher. In an embodiment, the method further comprises removing the at least one fluorescence quencher from the at least one fluorophore and the at least one polymer, thereby restoring fluorescence of the sensor.

In an embodiment, the analyte is suspected to contain at least one of: $Cu^+$, $Cu^{2+}$, and $Hg^{2+}$.

In another embodiment, a sensor comprises at least one fluorophore and at least one polymer wherein a change in sensor fluorescence is indicative of the presence of an analyte. In an embodiment, the sensor comprises a non-covalent complex of the at least one fluorophore and the at least one polymer. In an embodiment, the at least one polymer comprises a polymer capable of binding a metal ion. In an embodiment, the at least one polymer comprises an imidazole-containing polymer. In an embodiment, the imidazole-containing polymer comprises at least one of an N-vinylimidazole homo polymer and an N-vinylimidazole co-polymer.

In an embodiment the sensor further comprises at least one fluorescence quencher. In an embodiment, fluorescence of the sensor is restored in the presence of at least one analyte that removes the at least one quencher from the sensor. In an embodiment, the analyte comprises at least one of: $Cu^+$, $Cu^{2+}$, and $Hg^{2+}$.

In yet another embodiment, a system comprises a non-covalent complex of at least one fluorophore and at least one polymer capable of binding a metal ion, the at least one polymer capable of binding the metal ion further comprising at least one imidazole-containing polymer, an N-vinylimidazole homopolymer, and/or an N-vinylimidazole co-polymer. In an embodiment, the system further comprises at least one fluorescence quencher. In an embodiment, the fluorescence of the sensor is restored in the presence of at least one analyte that removes the at least one fluorescence quencher from the non-covalent complex of at least one fluorophore and the at least one polymer.

In an embodiment, the system the at least one polymer comprises at least one imidazole containing polymer, and the non-covalent complex further comprises luminol and $Cu^{2+}$ wherein the system is configured for chemiluminescence applications.

It will be appreciated that variations of the above-disclosed and other features and functions, or alternatives thereof, may be desirably combined into many other different systems or applications. Also, it should be understood that various presently unforeseen or unanticipated alternatives, modifications, variations or improvements therein may be subsequently made by those skilled in the art which are also intended to be encompassed by the following claims.

What is claimed is:

1. A sensing method comprising:
assembling a sensor comprising at least one non-fluorescent polymer and at least one fluorophore by mixing said at least one non-fluorescent polymer with said at least one fluorophore;
exposing said sensor to an analyte comprising $Cu^{2+}$; and
identifying a presence of said analyte according to a change in fluorescence of said sensor via formation of a non-covalent complex of said at least one fluorophore, said at least one non-fluorescent polymer, and the analyte, wherein said at least one fluorophore comprises luminol.

2. The method of claim 1 wherein said at least one non-fluorescent polymer comprises a polymer capable of binding a metal ion.

3. The method of claim 2 wherein said at least one non-fluorescent polymer capable of binding said metal ion comprises an imidazole-containing polymer.

4. The method of claim 1 wherein said at least one non-fluorescent polymer comprises at least one of:
an N-vinylimidazole homo polymer; and/or
an N-vinylimidazole co-polymer.

* * * * *